(12) United States Patent
Slade et al.

(10) Patent No.: US 8,957,242 B2
(45) Date of Patent: Feb. 17, 2015

(54) DUAL CATALYST ESTERIFICATION

(71) Applicant: Renewable Energy Group, Inc., Ames, IA (US)

(72) Inventors: David A. Slade, Ames, IA (US); Cody J. Ellens, Ankeny, IA (US); Jared N. Brown, Ankeny, IA (US); Anthony J. S. Pollard, Ames, IA (US); Bradley Neil Albin, Ames, IA (US)

(73) Assignee: Renewable Energy Group, Inc., Ames, IA (US)

( * ) Notice: Subject to any disclaimer, the term of this patent is extended or adjusted under 35 U.S.C. 154(b) by 0 days.

(21) Appl. No.: 14/203,885

(22) Filed: Mar. 11, 2014

(65) Prior Publication Data

US 2014/0275612 A1   Sep. 18, 2014

Related U.S. Application Data

(60) Provisional application No. 61/800,986, filed on Mar. 15, 2013.

(51) Int. Cl.
*C07C 67/08* (2006.01)

(52) U.S. Cl.
CPC ................................. *C07C 67/08* (2013.01)
USPC ........................................ 560/204; 560/129

(58) Field of Classification Search
USPC ................................................ 560/129, 204
See application file for complete search history.

(56) References Cited

U.S. PATENT DOCUMENTS

| | | |
|---|---|---|
| 4,698,186 A | 10/1987 | Jeromin |
| 5,536,856 A | 7/1996 | Harrison |
| 5,719,311 A | 2/1998 | Wu |
| 6,087,527 A | 7/2000 | Niwa |
| 6,355,817 B1 | 3/2002 | Woods |
| 7,550,614 B2 | 6/2009 | Banavali |
| 8,070,836 B2 | 12/2011 | Ng |
| 8,242,295 B2 | 8/2012 | Seki |
| 8,299,282 B2 | 10/2012 | Heinz |
| 2009/0294358 A1 | 12/2009 | Dietrich |
| 2010/0249442 A1 | 9/2010 | Heinz |
| 2010/0264015 A1 | 10/2010 | Portnoff |
| 2011/0054200 A1 | 3/2011 | Cai |
| 2012/0255223 A1 | 10/2012 | Kaul |

*Primary Examiner* — Sikarl Witherspoon
(74) *Attorney, Agent, or Firm* — Ryan N. Carter; Glenn Johnson

(57) ABSTRACT

Methods, processes, apparatus, equipment and systems are disclosed for converting carboxylic acids into esters by esterification with alcohol and a dual catalyst. The method combines a homogenous and heterogeneous catalyst in one or more reactors to increase the conversion of carboxylic acids compared to using a homogenous and/or heterogeneous catalyst independently. The invention converts free fatty acids into esters by esterification with alcohol and a dual catalyst such that the reaction mixture contains sufficiently low free fatty acids and the amount of free fatty acids in the product stream leaving the process remains stable over time.

28 Claims, 4 Drawing Sheets

DUAL CATALYST ESTERIFICATION

This application is based upon U.S. Provisional Application Ser. No. 61/800,986 filed on Mar. 15, 2013, the complete disclosure of which is hereby expressly incorporated by this reference.

FIELD OF THE INVENTION

The present invention generally relates to converting carboxylic acids into esters by esterification with alcohols in the presence of dual catalysts.

BACKGROUND OF THE INVENTION

Vegetable oils and animal fats and their by-products can contain considerable amounts of free fatty acids. Depending on the source of the raw material and level of processing or refining, free fatty acid (FFA) content may be between 0 and 100% by weight. When these materials are used for fatty acid alkyl ester (FAAE) production by base-catalyzed transesterification of mono-, di- and tri-acylglycerides (i.e., glycerides), the FFAs in the feed material are converted to soaps leading to yield losses and undesirable processing consequences (e.g., emulsion formation).

A pretreatment process may be used to reduce the FFA content in the raw materials (i.e., deacidify them) so that the glycerides can be converted to FAAEs in a base-catalyzed transesterification process. One method to reduce the FFA level in fats and oils is to remove them by distillation. This process can concentrate FFAs in a distillate stream to greater than 80 wt % while reducing the FFA level in the remaining fats and oils to as low as 0.1 wt % (or to an acid number of ~0.2 mg KOH/g). This process reduces the overall yield of feedstock to FAAE though and generates a stream of concentrated FFA that requires finding a new end-use, further processing or disposal. Another common method to remove small amounts of FFA is by adding a base reactant such as sodium hydroxide in order to saponify the FFA to soap which allows removal by water washing and filtration.

Another pretreatment process used to convert FFA into esters is acid catalyzed esterification. The FFA esterification reaction is affected by temperature, molar ratio of alcohol to FFA, mass transfer limitations, catalyst concentration, reaction time, and reaction stoichiometry. Since esterification reactions are reversible, the reaction does not go to completion. However, these equilibrium-limited reactions can be propelled further by increasing the concentration of the reactants or decreasing the concentration of the products. The reaction can be summarized as follows:

Equation 1

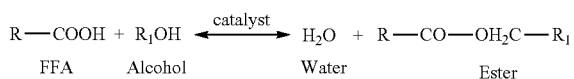

$$R\text{—}COOH + R_1OH \underset{}{\overset{catalyst}{\rightleftarrows}} H_2O + R\text{—}CO\text{—}OH_2C\text{—}R_1$$

FFA    Alcohol    Water    Ester where R and $R_1$ denote a hydrocarbon chain.

Because the equilibrium-limited reaction does not proceed to complete FFA conversion, the reaction is often conducted in two or more stages to achieve acceptable conversions (for example, greater than 99% conversion). Further FFA conversion can be accomplished by removing water from the reaction products either continuously or between reaction stages by distillation, flash evaporation, decanting or other such means. However, additional reaction stages require capital investment for additional unit operations as well as additional operating expenses. Esterification reactions can also be aided with excess alcohol and catalyst addition, although economic factors, small incremental improvements, and additional operational complexity usually limit their effectiveness. Esterification reactions can be performed in either batch or continuous process applications.

One such esterification process converts free fatty acids to FAAEs with alcohols using homogenous catalysis (catalyst and reactants have the same phase). Homogenous catalysis provides excellent selectivity and activity. Sulfuric acid, p-toluene sulfonic acid, and other strong acid catalysts have been used for esterification, but process equipment corrosion, product contamination, and catalyst recovery, neutralization, disposal, health and safety concerns and continuous cost issues remain—especially for conversion of renewable feedstocks with high FFA content into biofuels. Furthermore, we have observed that esterification with methanol using methanesulfonic acid (MSA) as an homogenous catalyst cannot reduce the initial FFA content significantly below 1 wt % in a single stage reaction regardless of initial FFA content unless uneconomical amounts of methanol and/or methanesulfonic acid are used in conjunction with extended residence time and/or high reaction temperature. Generally 1 wt % FFA content is undesirable for a base-catalyzed transesterification feedstock, and additional processing steps are therefore required.

Free fatty acids in raw materials can also be esterified with alcohols using heterogeneous catalysis (i.e., catalytic reactions wherein the reactants and catalyst are in different phases). Heterogeneous catalysis often provides good selectivity and, unlike most homogeneous catalysts, are designed to be used for extended periods of time, which avoids the continuous operating expense of unrecoverable homogeneous catalysts. However, heterogeneous esterification activity is generally less than with homogeneous catalysts, and multiple stages or extreme operating conditions are typically required to achieve acceptable conversions. Heterogeneous catalysis is employed on a global commercial scale in the petroleum chemicals and fuels industries, for example, in which extreme operating conditions are used.

One type of solid catalyst for esterification reactions, acidic ion exchange resin catalysts, has demonstrated promising results for acid esterification under relatively mild conditions, with conversions typically greater than 95% of the original FFA in a single stage reaction. However, there are unresolved concerns about catalyst fouling, durability, stability, activity, and replacement schedule with continuous use of commercial-grade higher FFA feedstocks. In fact, we have observed that at any initial amount of FFA, esterification with methanol using Amberlyst BD-20 ion exchange resin catalyst can briefly reduce the initial FFA content below approximately 1 wt % in a single stage by carefully selecting certain combinations of methanol ratio, weight hourly space velocity, and reaction temperature. However, the FFA conversion continually decreases over time with typical commercial-grade high FFA feedstocks. Potential causes of this steady deactivation include catalyst fouling and deactivation by proteins, phospholipids, metal ions, neutralization, chemical compounds (i.e. choline), precipitation, and stress mechanisms (physical, thermal, osmotic). Since such deactivation is not acceptable for commercial operation, new strategies must be developed to continuously maintain heterogeneous catalyst activity while simultaneously promoting the acid esterification reaction.

It is technically feasible to regenerate deactivated ion exchange catalyst with strong acids (hydrochloric, sulfuric, and possibly methane sulfonic). However, catalyst regeneration requires capital and operating expenditures for additional process units and typically cannot recover the initial level of activity. Furthermore, regeneration or catalyst replacement is a time-consuming and waste-generating activity which puts normal plant production on hold and adds costs for waste disposal.

What is needed in the art are methods that improve upon the respective challenges and disadvantages posed by homogenous and heterogeneous catalyst use for esterification of carboxylic acids. One method of esterification using a dual catalyst process produces a sufficiently low FFA product stream from a reactor with predictable and stable activity over time. A dual catalyst process can also reduce the continuous operating expense of using unrecoverable homogeneous catalysts by reducing the amount of homogeneous catalyst required to obtain the advantages of homogeneous catalyst use.

BRIEF DESCRIPTION OF THE DRAWINGS

The advantages of the technology described may be better understood by referring to the descriptions below with the accompanying drawings. The drawings are not to scale and represent exemplary configurations that depict general principles of the technology which are not meant to limit the scope of the invention. Dotted lines within the figures are representative of optional process streams which may be included as part of the process.

DETAILED DESCRIPTION OF EMBODIMENTS OF THE INVENTION

Figure 1:
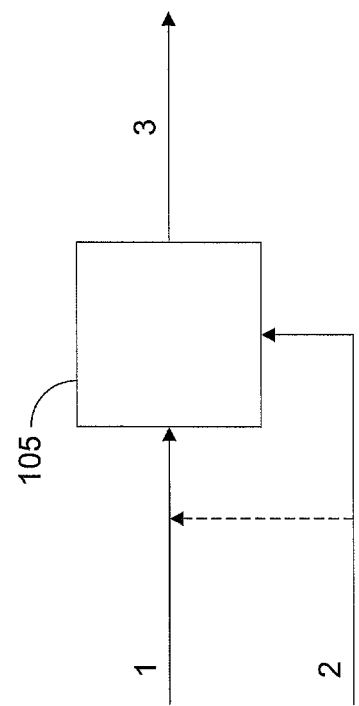
FIG. 1 describes an exemplary method for dual catalyst esterification of carboxylic acids whereby a feedstock containing free fatty acids enters a reactor containing a heterogeneous catalyst and excess alcohol with a homogenous catalyst that is either added directly to the reactor or optionally to the FFA-containing feedstock before it enters the reactor. After a prescribed residence time the reaction mixture exits the reactor having reduced free fatty acids compared to the feedstock entering the reactor.

The apparatus, devices, systems, and methods of the present invention will now be described in detail by reference to various non-limiting embodiments, including the figures which are exemplary only.

Unless otherwise indicated, all numbers expressing dimensions, capacities, and so forth used in the specification and claims are to be understood as being modified in all instances by the term "about." Without limiting the application of the doctrine of equivalents to the scope of the claims, each numerical parameter should at least be construed in light of the number of reported significant digits and by applying ordinary rounding techniques.

The present invention may be practiced by implementing process steps in different orders than as specifically set forth herein. All references to a "step" may include multiple steps (or substeps) within the meaning of a step. Likewise, all references to "steps" in plural form may also be construed as a single process step or various combinations of steps.

The present invention may be practiced by implementing process units in different orders than as specifically set forth herein. All references to a "unit" may include multiple units (or subunits) within the meaning of a unit. Likewise, all references to "units" in plural form may also be construed as a single process unit or various combinations of units.

As used in this specification and the appended claims, the singular forms "a," "an," and "the" include plural referents unless the context clearly indicates otherwise.

As used in this specification and the appended claims, the term "fats and oils" refers to any material of biological origin both vegetable and animal which is a useful feedstock for making fatty acid alkyl esters. These feedstocks may or may not have been pretreated using means understood by one skilled in the art to remove impurities. The term "carboxylic acid" is used to refer to mono-carboxylic acids, di-carboxylic acids, and other multi-carboxylic acids. The term "free fatty acid" refers to aliphatic carboxylic acids having carbon chains with 6 to 24 carbon atoms. Free fatty acids may be found in fats and oils between 0 to 100 wt % and form esters and water upon reacting with an alcohol under esterification conditions. The term "ester" is used to refer to organic esters, including mono-esters, di-esters, tri-esters, and more generally multi-esters. The term "alcohol" is used to refer to an organic alcohol, including monohydric alcohols, dihydric alcohols, and polyhydric alcohols generally.

Some variations of the present invention consist of a method of esterification using a dual catalyst process that produces a product stream with sufficiently low FFA in which the amount of FFA in the product stream leaving the process remains stable over time.

The methods of the invention can accommodate a wide range of feedstocks. In some embodiments of the invention, nonexclusive examples of feedstock are fats and oils including coconut oil, palm oils, palm kernel oil, cottonseed oil, rapeseed oil, peanut oil, olive oil, linseed oil, babassu oil, tea oil, Chinese tallow oil, olive kernel oil, meadowfoam oil, chaulmoorgra oil, coriander oil, canola oil, soybean oil, camelina oil, castor oil, pennycress oil, lard oil, jatropha oil, sunflower oil, algae oils, corn oil, used cooking oils, bacon grease, choice white grease, yellow grease, brown grease, poultry fat, beef tallow, lard, and fish oils. Additionally, feedstocks may include purified or distilled fats and oils including fatty acid distillates, palm fatty acid distillate, and others.

According to the invention in its most basic form, carboxylic acids are converted into esters by esterification with alcohol and a dual catalyst. One method (100) of the invention, with reference to FIG. 1, involves introducing a feedstock containing carboxylic acid (1) to a reactor (105) containing heterogeneous catalyst and simultaneously introducing an alcohol and a homogenous catalyst (2) either to the reactor (105) or optionally to the feedstock containing carboxylic acid (1) before entering the reactor (105). After a prescribed residence time and set of operating conditions the reaction mixture (3) exits the reactor (105) containing less carboxylic acid than the feedstock (1).

In one embodiment, the feedstock containing carboxylic acid (1) is pretreated to remove impurities and dried to remove moisture before entering the reactor (105). In one embodiment, alcohol (2) is introduced to a feedstock containing carboxylic acid (1) and homogenous catalyst. In another embodiment the homogenous catalyst is introduced to the reactor (105) separately from the alcohol (2) and the feedstock containing carboxylic acid (1).

In one embodiment, the amount of homogenous catalyst introduced to a reactor (105) is between 0 wt % and 8 wt % of the feedstock (1) entering the reactor (105). In another embodiment, the amount of homogenous catalyst introduced to a reactor (105) is between 0.01 wt % and 5 wt % of the feedstock (1) entering the reactor (105). In yet another embodiment, the amount of homogenous catalyst introduced to a reactor (105) is between 0.05 wt % and 1.5 wt % of the feedstock (1) entering the reactor (105).

The reaction is conducted using at least a stoichiometric amount of alcohol as determined on an FFA basis according to Equation 1. In one embodiment the reaction is conducted using a 0.2 to 30 molar excess of alcohol depending on the feedstock carboxylic acid content and alcohol rectification capacity. Alcohol levels greater than 30 molar excess typically provide minimal benefit for first stage reactions, although in some embodiments greater than 30 molar excess may be desirable.

The reaction should take place under sufficient pressure to maintain the alcohol in a liquid state at the desired reaction temperature. In some situations the pressure may be below the vapor pressure of the alcohol although the alcohol may reflux back into the reaction mixture. Pressure is generally maintained at a constant level throughout the reaction. In one embodiment the pressure is maintained between 0 and 150 psig. In another embodiment, the reaction pressure is maintained between 1 and 100 psig.

The reaction should take place at an elevated temperature to improve reaction kinetics. In one embodiment the temperature is between 50 and 150° C. In another embodiment, the temperature is maintained between 60 and 110° C. The reaction temperature may be maintained by electric heat, steam, thermal fluid or other such industrial means practiced by one skilled in the art.

The reactor (105) should be sized to provide sufficient residence time for the carboxylic acid contained in the feedstock (1) to be converted sufficiently to esters. In one embodiment the apparent residence time of reactants in the heterogeneous catalyst bed is between 2 and 480 minutes. In another embodiment, the residence time is between 5 and 120 minutes. In yet another embodiment, the residence time is between 10 and 60 minutes.

The reactor (105) contains a predetermined amount of heterogeneous catalyst. In one embodiment, the quantity of heterogeneous catalyst is selected to achieve a desired weight hourly space velocity (WHSV) given in units of $g_{carboxylic\ acid} \cdot hr^{-1}/g$ heterogeneous catalyst. In one embodiment, the WHSV is selected between 0.1-8.0 $g_{carboxylic\ acid} \cdot hr^{-1}/g$ heterogeneous catalyst depending on the carboxylic acid contained in the feedstock (1). In another embodiment, the WHSV is selected between 0.2-5.0 $g_{carboxylic\ acid} \cdot hr^{-1}/g$ heterogeneous catalyst depending on the carboxylic acid contained in the feedstock (1).

The reactor (105) may be configured and oriented in a number of ways. It (105) may be a continuously-stirred tank, plug-flow, tubular-flow, mixed-flow, fixed bed, fluidized bed, batch, semi-batch, recirculating, or other reactor type. The reactor (105) may be oriented either horizontally or vertically. In a vertical configuration, the reactants may flow upwards or downwards through the reactor (105). The reactor (105) may have freeboard space above the catalyst bed to allow for catalyst movement and expansion as known to those skilled in the art. The reactor may be fitted with provisions to add and remove heterogeneous catalyst, including by means of motive fluid flow.

In one embodiment, method (100) in FIG. 1 is conducted as a single operation. In another embodiment method (100) is repeated in series with method (100). In another embodiment method (100) is conducted in parallel with method (100). In another embodiment method (100) is repeated one or more times in series or parallel with method (100).

Figure 2:
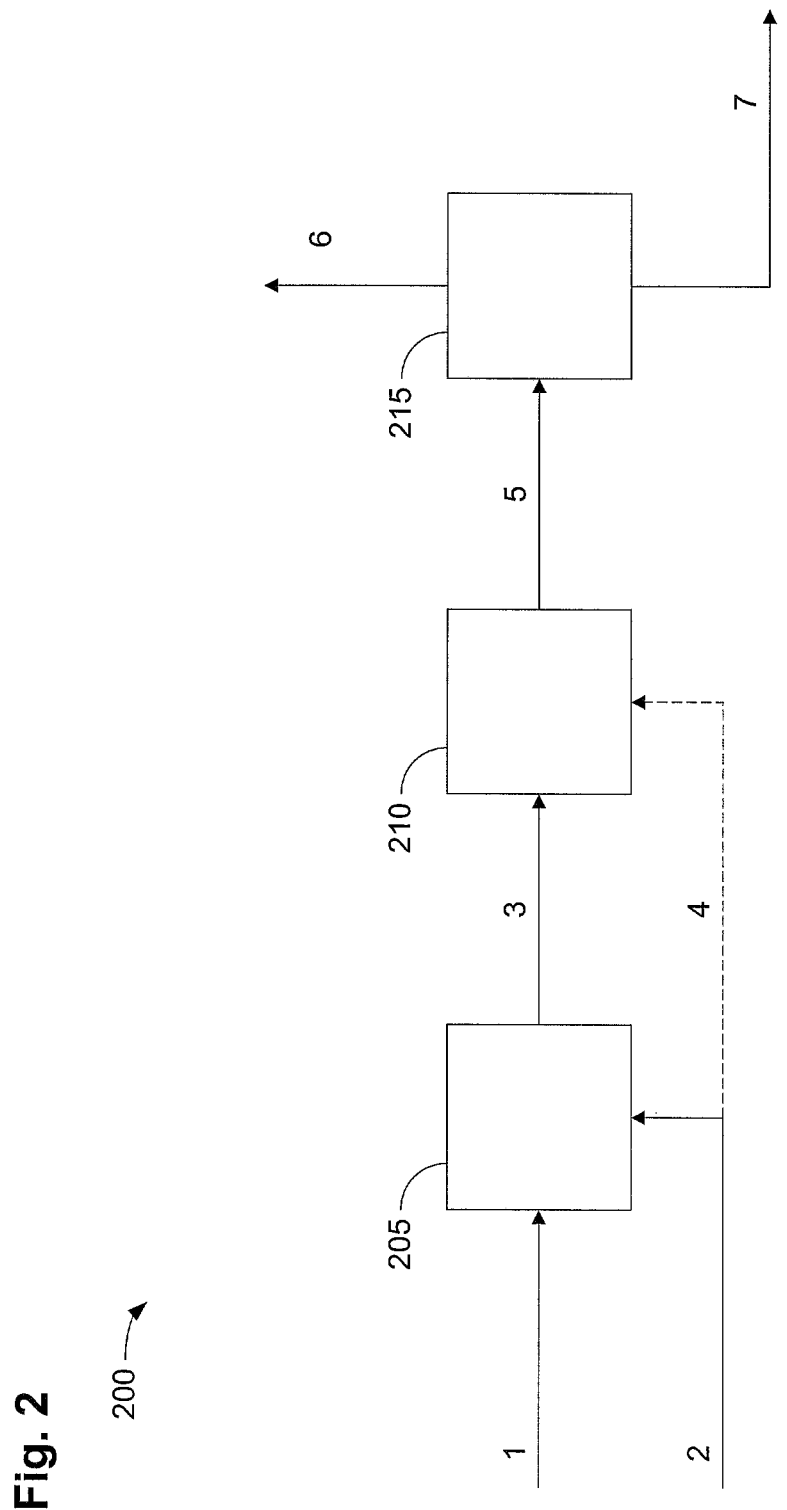
FIG. 2 describes an exemplary method for dual catalyst esterification of free fatty acids whereby a homogenous catalyst and excess alcohol are first added to a feedstock containing FFA and after some prescribed residence time and set of operating conditions the first reaction mixture enters a reactor containing a heterogeneous catalyst where additional alcohol and homogenous catalyst may optionally be added. After a prescribed residence time and set of operating conditions the second reaction mixture exits the reactor with reduced free fatty acids and enters a separation stage.

Another method (200) of the invention, with reference to FIG. 2, involves introducing a feedstock containing carboxylic acid (1) and an alcohol and a homogenous catalyst (2) to unit (205). Unit (205) may be an inline mixer, stirred tank, continuously stirred-tank reactor or other such unit operation depending on the desired operating conditions as determined by someone skilled in the art.

A first reaction mixture (3) containing lower quantities of carboxylic acid than the feedstock (1) exits unit (205) and enters a reactor (210) containing heterogeneous catalyst. Optionally, an additional amount of alcohol and/or homogenous catalyst (4) is added to the reactor (210).

After a prescribed residence time a second reaction mixture (5) exits the reactor (210) containing lower quantities of carboxylic acid than both the feedstock (1) and the first reaction mixture (3). The second reaction mixture (5) enters unit (215) which may be a decanter, centrifuge, flash evaporator, flash drum, vacuum distillation column, or other similar separation unit. Depending on the unit operation desired, unit (215) may operate at temperatures and pressures above or below atmospheric conditions.

In one embodiment, alcohol, water, and other volatiles (6) are removed from the second reaction mixture (5) contained in unit (215) by distillation leaving a dry reaction mixture (7) (also referred to herein as the oil phase) that may contain a portion of homogenous catalyst. In another embodiment, a portion of alcohol, water, and homogenous catalyst (6) are removed from the second reaction mixture (5) contained in unit (215) by decantation or centrifugation, leaving a principally dry reaction mixture (7). In one embodiment, operating conditions of unit (215) are selected to minimize the amount of homogenous catalyst in stream (6) thereby maximizing the amount of the homogenous catalyst in stream (7). In one embodiment the second reaction mixture (5) is washed with water before entering a decanter (215). In any embodiment, dry reaction mixture (7) may continue to a transesterification process, alcohol may be recovered from stream (6) and a portion of homogenous catalyst may be recovered from either stream (6) or (7). In any embodiment it may be preferable to minimize the amount of moisture in stream (7).

In one embodiment, the feedstock containing carboxylic acid (1) is pretreated to remove impurities and dried to remove moisture before entering the reactor (205). In one embodiment, feedstock containing carboxylic acid (1) and also containing homogenous catalyst and alcohol (2) is introduced to the reactor (205). In one embodiment the homogenous catalyst is introduced to the reactor (205) separately from the alcohol (2) and the feedstock containing carboxylic acid (1).

In one embodiment, the operating conditions in units (205) and (210) are substantially similar to those described previously for unit (105). In one embodiment, the reaction time in unit (205) is around 1-120 minutes, and in another embodiment the reaction time is around 5-35 minutes. In a different embodiment, the temperature, residence time, alcohol to FFA molar ratio, and other operating conditions are different for unit (205) and unit (210). For instance it may be desirable to divide a fixed quantity of alcohol between unit (205) and unit (210), with either equal or unequal portions of alcohol routed to each unit.

Figure 3:
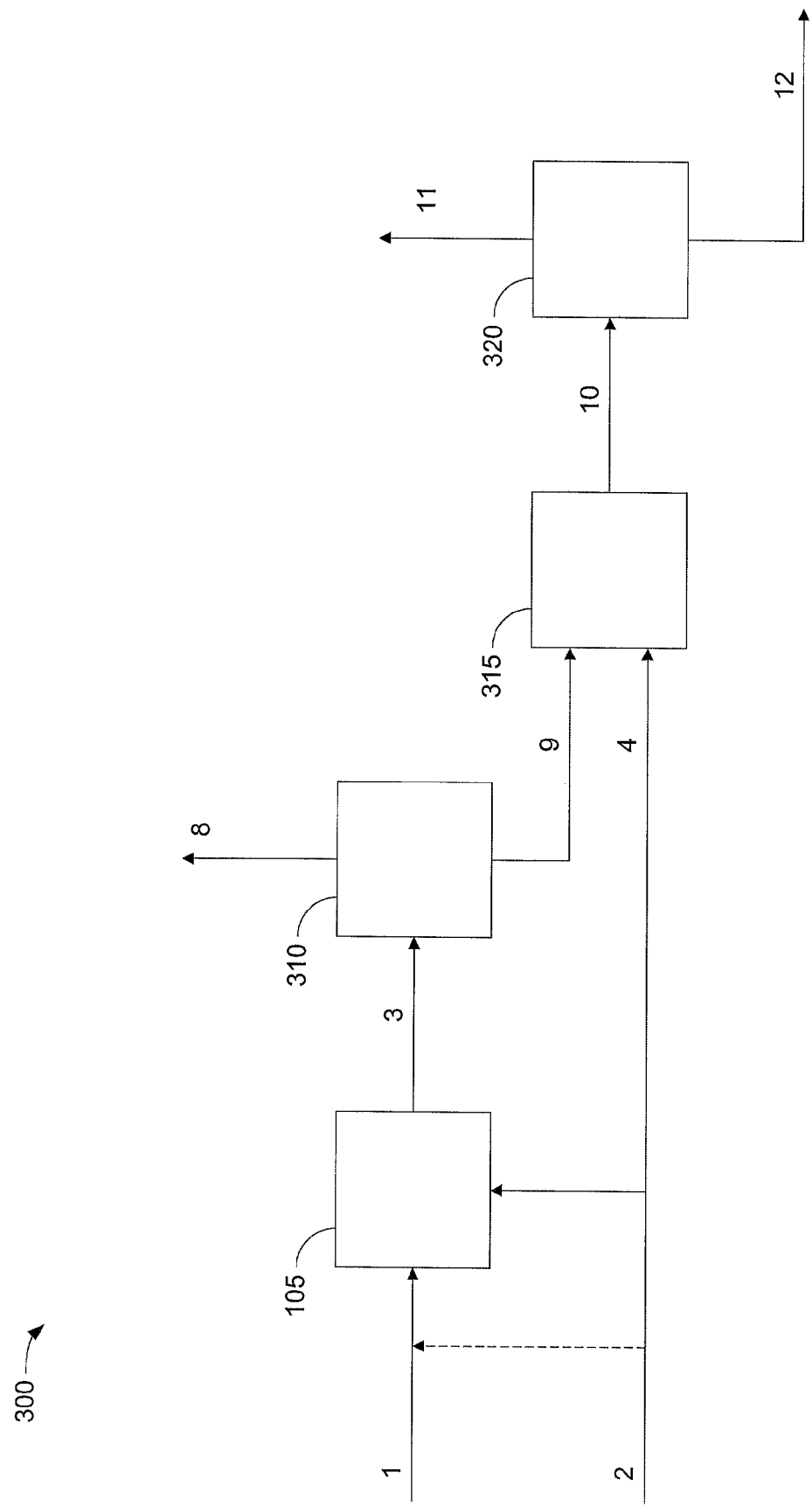
FIG. 3 describes an exemplary method for dual catalyst esterification of free fatty acids whereby a feedstock containing free fatty acids enters a first reactor followed by a first separation stage and subsequently a second reactor and second separation stage. The final reaction mixture has reduced free fatty acids compared to the feedstock entering and to the reaction mixture leaving the first reactor.

Another method (300) of the invention, with reference to FIG. 3, involves introducing a feedstock containing carboxylic acid (1) to a first reactor (105) containing heterogeneous catalyst and simultaneously introducing an alcohol and a homogenous catalyst (2) either to the reactor (105) or optionally to the feedstock containing carboxylic acid (1) before entering the first reactor (105). The operating conditions and provisions of the first reactor (105) are as previously described. After a prescribed residence time a first reaction mixture (3) exits the first reactor (105) containing lower quantities of carboxylic acid than the feedstock (1). The first reaction mixture (3) enters unit (310) which may be a decanter, centrifuge, flash drum, vacuum distillation column or other separation unit. In one embodiment, alcohol and water and other volatiles (8) are removed from the first reaction mixture (3) contained in unit (310) by distillation leaving a dry reaction mixture (9) and a portion of homogenous catalyst. In another embodiment, a portion of alcohol, water and homogenous catalyst (8) are removed from the first reaction mixture (3) contained in unit (310) by decantation or centrifugation, leaving a principally dry reaction mixture (9). It may be desirable to operate unit (310) to minimize the amount of homogenous catalyst in stream (8) thereby maximizing the amount of the homogenous catalyst in stream (9). In one embodiment the first reaction mixture (3) is washed with water before entering a decanter (310). In any embodiment it may be desirable to minimize the amount of moisture in stream (9). In any embodiment, dry reaction mixture (9) proceeds to a second reactor (315) which may or may not contain heterogeneous catalyst. Additional homogenous catalyst is optionally added with alcohol (4) to the second reactor (315). After a prescribed residence time a second reaction mixture (10) exits the second reactor (315) containing lower quantities of carboxylic acid than the feedstock (1) and first reaction mixture (3). In one embodiment, unit (315) may have operating conditions and provisions as previously described for unit (105) when charged with heterogeneous catalyst; whereas unit (315) may have operating conditions and provisions as described for unit (205) when not containing heterogeneous catalyst. The second reaction mixture (10) enters unit (320) which may be a decanter, centrifuge, flash evaporator, flash drum, vacuum distillation column or other separation unit. In one embodiment, alcohol and water and other volatiles (11) are removed from the second reaction mixture (10) contained in unit (320) by distillation leaving a dry reaction mixture (12) and a portion of homogenous catalyst. In one embodiment, a portion of alcohol, water and homogenous catalyst (11) are removed from the second reaction mixture (10) contained in unit (320) by decantation, leaving a principally dry reaction mixture (12). In one embodiment, the second reaction mixture (10) is washed with water before entering a decanter (320). In one embodiment it may be beneficial to minimize the amount of homogenous catalyst in stream (12). In any embodiment, dry reaction mixture (12) may continue to a transesterification, hydrogenation or other catalytic chemical conversion process, alcohol may be recovered from stream (11) and a portion of homogenous catalyst may be recovered from either stream (11) or (12).

In one embodiment, the feedstock described in the invention is dried to a moisture content of less than 0.2 wt % and has been pretreated with filters and centrifugation to minimize the amount of physical and chemical foulants present in the feedstock. In one embodiment the carboxylic acids contained in the feedstock are free fatty acids. In one embodiment, the alcohol described in the invention is dry methanol. In one embodiment, the homogenous catalyst described in the invention is methanesulfonic acid (MSA). However, other homogenous catalysts may be used including sulfuric or phosphoric acid. In one embodiment, the heterogeneous catalyst described in the invention is an ion exchange resin catalyst with sulfonic acid groups such as Amberlyst BD20 sulfonic acid ion exchange resin from Rohm and Haas and Lewatit® catalyst from Lanxess. In one embodiment, other heterogeneous catalysts may be used including the DOWEX dry acid catalysts from DOW such as DR-2030 or M-31.

In one embodiment the FFA content of the reaction mixture is maintained at a sufficiently low level to enter a catalytic transesterification or hydrotreating process without requiring an intermediate FFA removal step. In one embodiment the FFA content of the reaction mixture is consistently below 0.5 wt %. In another embodiment the FFA content is consistently below 0.3 wt %.

In one embodiment the feedstock containing carboxylic acid is pretreated to remove excess water and impurities. The pretreatment steps may include drying, filtering (including in-line sock filters, ceramic membrane filters, absorbent media, etc.), centrifugation, or other similar techniques known to those skilled in the art. Additionally, prior to any reaction vessels described in this invention, in one embodiment the pretreated feedstock is passed through a bed of ion exchange resin for the purpose of removing impurities that may deactivate our foul the heterogeneous catalyst. Without limiting the scope of the invention, one such resin is Amberlyst BD-19. One or more guard beds may be employed in series or parallel.

In one embodiment there may be multiple reactors arranged in a way to allow for taking one (or more) reactor (s) offline while the heterogeneous catalyst in one or more different reactor(s) is regenerated. For acidic cation exchange resins, the catalyst may be regenerated with an acid such as hydrochloric acid (4%-10%), sulfuric acid (1-5%), or methane sulfonic acid (1-10%). In general about 2.5-12 lb of regenerant is required per $ft^3$ of catalyst. In one embodiment the regenerating acid flow in the opposite direction (countercurrent) of the service flow, noting the service flow may be upwards or downwards through the reactor. The temperature at regeneration should range from approximately 30-60° C. The residence time of the acid though the catalyst bed should be approximately 20-40 minutes. The regeneration may be performed in multiple steps with different acid concentrations and residence times in each step.

In one embodiment, the final reaction mixture (3), (5), or (10) is separated into an alcohol and water phase and an oil phase (also referred to herein as the dry reaction mixture). The homogenous catalyst may be contained in either or both phases. The final reaction mixture (3), (5), or (10) may be dried and/or separated by distillation, flash evaporator, flash drum, molecular sieves, ceramic membranes, decanters, centrifuges or other such means to remove water, alcohol and acid catalyst to obtain the oil phase. These steps can occur in different vessels in multiple stages according to one skilled in the art.

In one embodiment the oil phase is sufficiently dry, free of water, alcohol and homogenous catalyst before entering a transesterification process or a crude biodiesel purification process.

Without limiting the scope of the invention, it is theorized that some esterification catalysts, particularly ion exchange resin catalysts tend to foul or become deactivated due to metal ions, proteins, phospholipids, chemical compounds (i.e. choline), neutralization, precipitation, stress mechanisms (physical, thermal, osmotic), etc. Such contaminants can be introduced by the feedstock, corrosion, and other impurities or mechanism within the process. It is possible that these contaminants foul the catalyst active sites by neutralization, chemical deactivation, absorption, and adsorption. For a variety of feedstocks and experimental conditions increasing product FFA trends have been observed with Amberlyst ion exchange resin catalyst supporting the catalyst deactivation theory. Since the fouling and deactivation phenomenon occurs gradually and is dependent on feedstock contaminant concentration, sufficient time is needed to observe increasing product FFA trends.

However, adding the homogenous catalyst to the feedstock before the reaction mixture reaches the heterogeneous catalyst or into the heterogeneous catalyst reactor: 1) eliminates the increasing product FFA trend observed with Amberlyst BD-20 sulfonic acid ion exchange resin catalyst and 2) reduces the final FFA content compared to reacting the same feedstock under similar reaction conditions with either methanesulfonic acid or Amberlyst BD-20 sulfonic acid ion exchange resin independently. In addition to the direct activity of the homogeneous catalyst, it is believed that a portion of the homogeneous catalyst prevents the contaminants from binding to the heterogeneous catalyst and thereby prevents fouling or deactivation of the heterogeneous catalyst. This maintains a higher number of active sites in the heterogeneous catalyst for FFA esterification resulting in lower overall product FFA content. Therefore, in one embodiment of this invention, the final FFA content of the reaction mixture leaving the process during steady state operation remains stable over time, that is, the final FFA content does not consecutively increase or decrease so as to create a trend.

The invention is illustrated in detail below with reference to the examples, but without restricting it to them.

EXAMPLES

Example 1

Conversion of Free Fatty Acids with a Heterogeneous Catalyst

Figure 4:
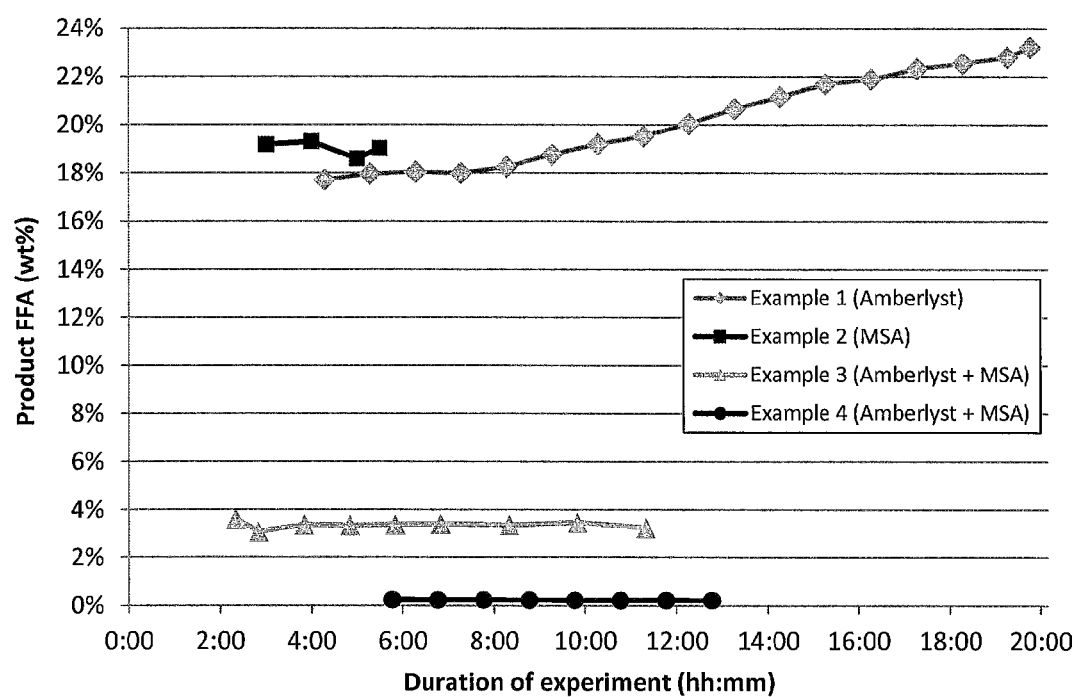
FIG. 4 is a chart showing the product of free fatty acid content for various experiments from a continuous flow reactor.

Fatty acid distillate with a free fatty acid content of 84.5 wt % was passed through a static mixer and upwards through a fixed bed reactor at 1.39 g/min with 1.13 g/min dry methanol. The calculated molar ratio of methanol to free fatty acids was 8.51. The reaction took place at 80° C., a pressure of 60 psig and an apparent residence time of 22 minutes through a fixed bed containing 25.71 g of dry Amberlyst BD-20 sulfonic acid ion exchange resin catalyst as indicated in Table 1. The catalyst particles were fixed in a customized stainless steel reactor having 0.76" inner diameter and 15" bed height. The flowrates provide a liquid hourly space velocity of 2.73 $hr^{-1}$ and a weight hourly space velocity of 2.73 $hr^{-1}$. Approximately 1.66 kg of feedstock was fed over 20 hours. Sample FFA quantity was determined using a Metrohm Titrando 836 titration setup. Reaction mixture samples were water washed and centrifuged for 5 minutes in 10 mL centrifuge tubes to remove water and methanol to obtain the oil phase. The oil phase was pipetted off the top, heated to 65° C. and mixed with 75 mL of lab-grade 2-propanol before titrating. Potassium hydroxide (KOH) was added to titrate the FFA. The final FFA calculation assumed 282 g/mol as the molecular weight of FFA and used a pH endpoint to determine titrant volume. The final FFA content of the oil phase began at 17.71 wt % and ended up at 23.21 wt % over the duration of the FFA testing (16.5 hours) as shown in FIG. 4. The final product FFA amount in the oil phase represents a reduction of 73% over the feedstock.

TABLE 1

Experimental operating conditions and results

| | Example 1 | Example 2 | Example 3 | Example 4 |
|---|---|---|---|---|
| Feedstock | Fatty Acid Distillate | Fatty Acid Distillate | Fatty Acid Distillate | Corn oil |
| Heterogeneous catalyst | Amberlyst BD-20 | — | Amberlyst BD-20 | Amberlyst BD-20 |
| Homogenous catalyst | — | MSA | MSA | MSA |
| Feedstock FFA (% wt) | 84.50% | 88.10% | 90.90% | 10.40% |
| Nominal temperature (° C.) | 80 | 80 | 80 | 80 |
| Nominal pressure (psig) | 60 | 60 | 60 | 60 |
| Feedstock flow rate (g/min) | 1.39 | 1.19 | 1.13 | 1.74 |
| Methanol flow rate (g/min) | 1.13 | 1.14 | 1.13 | 0.51 |
| Methanol:FFA molar ratio | 8.51 | 9.62 | 9.72 | 24.8 |
| Apparent residence time (min) | 22 | — | 24.4 | 25.3 |
| Homogenous catalyst contact time (min) | — | 24.7 | 70.8 | 73.4 |
| $WHSV^A$ ($g_{FFA} \cdot hr^{-1}/g_{dry\ catalyst}$) | 2.73 | — | 2.39 | 0.42 |
| LHSV ($mL_{Total\ flow} \cdot hr^{-1}/mL_{reactor}$) | 2.73 | 2.34 | 2.46 | 2.38 |
| MSA concentration (fat basis) | — | 0.48% | 0.50% | 0.15% |
| Final product FFA (% wt) | 23.2% | 19.0% | 3.4% | 0.2% |
| FFA reduction (%) | 73% | 78% | 96% | 98% |

A – for heterogeneous catalyst only.

Example 2

Conversion of Free Fatty Acids with Homogenous Catalyst

Fatty acid distillate with a free fatty acid content of 88.1 wt % was passed through a static mixer and stainless steel tubing (no packed bed of heterogeneous catalyst) at 1.19 g/min with 1.14 g/min dry methanol containing 0.48 wt % methanesulfonic acid (feedstock basis). The calculated molar ratio of methanol to free fatty acids was 9.62. The reaction took place at 80° C., a pressure of 60 psig having an apparent residence time of 24.7 minutes as indicated in Table 1. The flowrates provide a liquid hourly space velocity of 2.34 hr$^{-1}$. Approximately 453 g of feedstock was fed over 6.4 hours. FFA testing of the dry reaction mixture was completed as described in Example 1 except that a double water wash was performed to remove all MSA. The final average FFA content of the dry reaction mixture was 19.04±0.31 wt % over the duration of FFA testing (2.5 hours) as shown in FIG. 4. The final product FFA amount represents a reduction of 78% over the feedstock.

Example 3

Conversion of Free Fatty Acids with Dual (Heterogeneous and Homogenous) Catalysts Fatty acid distillate with a free fatty acid content of 90.9 wt % was passed through a static mixer and upwards through a fixed bed reactor at 1.13 g/min of a with 1.13 g/min dry methanol containing 0.50 wt % methanesulfonic acid (feedstock basis). The calculated molar ratio of methanol to free fatty acid was 9.72. The reaction took place at 80° C., a pressure of 60 psig having an apparent residence time of 24.4 minutes through a fixed bed containing 25.71 g of dry Amberlyst BD-20 sulfonic acid ion exchange resin catalyst as indicated in Table 1. The catalyst particles were fixed in a customized stainless steel reactor having 0.76" inner diameter and 15" bed height. This equates to a liquid hourly space velocity of 2.46 hr$^{-1}$ and a weight hourly space velocity of 2.39 hr$^{-1}$. The total contact time of feedstock and methanol with MSA was approximately 70 minutes. Approximately 766 g of feedstock was fed over 11.3 hours. The FFA testing was completed as described in Example 2. The final average FFA content of the dry reaction mixture was 3.35±0.12 wt % over the duration of FFA testing (8.5 hours) as shown in FIG. 4. The final product FFA amount represents a reduction of 96% over the feedstock. Comparing Example 1 and 2 it is clear the added MSA has two effects: decreasing the final FFA content and maintaining a constant FFA level in the product stream from a continuous flow reactor.

Example 4

Conversion of Free Fatty Acids with Dual (Heterogeneous and Homogenous) Catalysts Inedible corn oil with a free fatty acid content of 10.4 wt % was passed through a static mixer and upwards through a fixed bed reactor at 1.74 g/min with 0.51 g/min dry methanol containing 0.23 wt % methanesulfonic acid (feedstock basis). The calculated molar ratio of methanol to free fatty acid was 24.8. The reaction took place at 80° C., a pressure of 60 psig having an apparent residence time of 25.3 minutes through a fixed bed containing 25.71 g of dry Amberlyst BD-20 sulfonic acid ion exchange resin catalyst as indicated in Table 1. The catalyst particles were fixed in a customized stainless steel reactor having 0.76" inner diameter and 15" bed height. This equates to a liquid hourly space velocity of 2.38 hr$^{-1}$ and a weight hourly space velocity of 0.42 hr$^{-1}$. The total contact time of feedstock and methanol with MSA was approximately 73 minutes. Approximately 1.36 kg of feedstock was fed over 13 hours. The FFA testing was completed as described in Example 2. The final average FFA content of the dry reaction mixture was 0.234±0.004 wt % over the duration of the test (6 hours) as shown in FIG. 4. The final product FFA amount represents a reduction of 98% over the feedstock.

In this description, reference has been made to multiple embodiments and to the accompanying drawings in which are shown by way of illustration specific exemplary embodiments of the invention. These embodiments are described in sufficient detail to enable those skilled in the art to practice the invention, and it is to be understood that modifications to the various disclosed embodiments may be made by a skilled artisan.

Where methods and steps described above indicate certain events occurring in certain order, those of ordinary skill in the art will recognize that the ordering of certain steps may be modified and that such modifications are in accordance with the principles of the invention. Additionally, certain steps may be performed concurrently in a parallel process when possible, as well as performed sequentially.

All publications, patents, and patent applications cited in this specification are herein incorporated by reference in their entirety as if each publication, patent, or patent application were specifically and individually put forth herein.

The embodiments, variations, and figures described above provide an indication of the utility and versatility of the present invention. Other embodiments that do not provide all of the features and advantages set forth herein may also be utilized, without departing from the spirit and scope of the present invention. Such modifications and variations are considered to be within the scope of the principles of the invention defined by the claims.

What is claimed is:

1. A method for producing esters, comprising:
providing an alcohol from an alcohol source;
providing a feedstock from a feedstock source, wherein the feedstock has a carboxylic acid content; and
reacting the alcohol and the feedstock in a reactor with a homogenous catalyst and a heterogeneous catalyst to produce a reaction mixture having a carboxylic acid content which is lower than the carboxylic acid content of the feedstock, wherein the homogenous catalyst and the heterogeneous catalyst each have an activity.

2. The method of claim 1, wherein said carboxylic acid content of the feedstock is between 0.1 wt % and 100 wt % carboxylic acids.

3. The method of claim 2, wherein said carboxylic acids are free fatty acids.

4. The method of claim 1, wherein said alcohol is methanol or ethanol.

5. The method of claim 1, wherein said heterogeneous catalyst is an ion exchange resin catalyst.

6. The method of claim 1, wherein said homogenous catalyst comprises one of methanesulfonic acid, sulfuric acid, phosphoric acid, and p-toluene sulfonic acid.

7. The method of claim 1, wherein said reactor is a fixed bed reactor.

8. The method of claim 1, wherein the feedstock, alcohol, and homogeneous catalyst flow upward through said reactor.

9. The method of claim 1, wherein the feedstock, alcohol, and homogeneous catalyst flow downward through said reactor.

10. The method of claim 1, wherein said homogenous catalyst prolongs the activity of said heterogeneous catalyst.

11. The method of claim 1, wherein the combination of said homogeneous catalyst and said heterogeneous catalyst provide increased conversion relative to the use of either catalyst alone.

12. The method of claim 1, wherein the reactor is a continuous flow reactor.

13. The method of claim 1, further comprising the step of separating a majority of the alcohol and water from the reaction mixture to obtain a dry reaction mixture.

14. The method of claim 13, wherein the dry reaction mixture is a principally dry reaction mixture.

15. The method of claim 13, wherein the reactor is a continuous flow reactor.

16. The method of claim 1, wherein the reaction mixture has a free fatty acid content below 0.5 wt %.

17. The method of claim 1, wherein the reaction mixture has a free fatty acid content below 0.3 wt %.

18. The method of claim 1, further comprising the step of processing the reaction mixture in one of a transesterification process and a hydrotreating process.

19. A method for producing esters comprising:
providing an alcohol from an alcohol source;
providing a feedstock from a feedstock source, wherein the feedstock has a carboxylic acid content;
reacting the alcohol and the feedstock in a first reactor with a homogenous catalyst to produce a first reaction mixture; and
reacting the first reaction mixture in a second reactor with a heterogeneous catalyst to produce a second reaction mixture having a carboxylic acid content which is lower than the carboxylic acid content of the feedstock.

20. The method of claim 19, wherein said second reaction mixture has a free fatty acid content below 0.5 wt %.

21. The method of claim 19, further comprising the step of processing the second reaction mixture in one of a transesterification process and a hydrotreating process.

22. A method for producing esters comprising:
providing an alcohol from an alcohol source;
providing a feedstock from a feedstock source, wherein the feedstock has a carboxylic acid content;
reacting the alcohol and the feedstock in a first reactor with a homogenous catalyst and a heterogeneous catalyst to produce a first reaction mixture having a carboxylic acid content which is lower than the carboxylic acid content of the feedstock; and
separating the first reaction mixture into a first stream comprising a majority of water and alcohol and a second stream comprising a dry reaction mixture.

23. The method of claim 22 wherein the dry reaction mixture is a principally dry reaction mixture.

24. The method of claim 22, wherein said first reaction mixture is separated by distillation, flash evaporator, flash drum, decantation, molecular sieve or centrifugation.

25. The method of claim 22, further comprising the step of reacting the second stream in a second reactor with at least one of additional homogeneous catalyst, additional heterogeneous catalyst, and additional alcohol to form a second reaction mixture.

26. The method of claim 25, further comprising the step of processing the second reaction mixture in one of a transesterification process and a hydrotreating process.

27. A method for producing esters comprising:
reacting an alcohol with a feedstock containing carboxylic acids in the presence of both a homogenous and heterogeneous catalyst to form a reaction mixture, wherein said reaction mixture is further reacted in a second reactor forming a second reaction mixture.

28. The method of claim 27, wherein at least one of additional alcohol and additional homogenous catalyst is added to said second reactor.

* * * * *